US006433172B1

(12) United States Patent
Grondard et al.

(10) Patent No.: US 6,433,172 B1
(45) Date of Patent: Aug. 13, 2002

(54) STEROESPECIFIC PREPARATION OF CHIRAL 1-ARYL- AND 1-HETEROARYL-2-SUBSTITUTED ETHYL-2-AMINES

(75) Inventors: Luc Grondard, Courcouronnes; Jean-Paul Casimir, Ermont; Patrick Leon, Tassin la Demi Lune, all of (FR); Michael K. O'Brien, Berwyn; Matthew R. Powers, Barto, both of PA (US); Daniel Robin, Crosne (FR)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/426,403

(22) Filed: Oct. 25, 1999

Related U.S. Application Data

(62) Division of application No. 09/266,641, filed on Mar. 11, 1999, now Pat. No. 6,127,550, which is a continuation of application No. PCT/US97/15729, filed on Sep. 10, 1997.
(60) Provisional application No. 60/026,005, filed on Sep. 12, 1996.

(51) Int. Cl.[7] .................... C07D 221/18; C07D 203/04; C07C 303/00; C07C 307/00
(52) U.S. Cl. .................... 546/75; 548/965; 564/80; 564/84; 564/92
(58) Field of Search .................... 548/965; 564/80, 564/84, 92; 546/75

(56) References Cited

U.S. PATENT DOCUMENTS 3,431,152 A * 3/1969 Hauser et al. .............. 548/965
4,933,470 A  6/1990 Jones
5,364,862 A  11/1994 Spada et al.

OTHER PUBLICATIONS

CA123:169444, Toshimitsu et al, 1995.*

CA127:175995, Maligres et al, 1997.*

CA 86:155431, 1976.*

Kiso et al., Efficient Removal of Protecting Groups by a 'Push–Pull' Mecanism. II. Deprotection of O–Benzyltyrosine with a Thioanisol–Trifluoroacetic Acid System without O–to–C Rearrangements., Chem. Pharm. Bull. 28(2):673–676 (1980).

Kitagawa et al., Studies on Peptides LXXXV. A New Deprotecting Procedure for p–Toluenesulfonyl and p–Methoxybenzenesulfonyl Groups from the Nim–Function of Histidine., Chem. Phar. Bull. 28(3):926–931 (1980).

Yajima et al., Studies on Peptides. LXXX. NG–Mestylene–2–sulfonylarginine, Chem. Pharm. Bull. 26(12):3752–3757 (1978).

* cited by examiner

*Primary Examiner*—Deborah C. Lambkin
(74) *Attorney, Agent, or Firm*—Paul R. Darkes; William C. Coppola; Ross J. Oehler

(57) ABSTRACT

This invention is directed to methods for stereospecifically preparing [(1-optionally substituted aryl)- or (1-optionally substituted heteroaryl)]-2-substituted ethyl-2-amines, having chirality at the 2-position, and to intermediates to the substituted ethyl-2-amines.

25 Claims, No Drawings

STEREOSPECIFIC PREPARATION OF CHIRAL 1-ARYL- AND 1-HETEROARYL-2-SUBSTITUTED ETHYL-2-AMINES

This application is a divisional application of U.S. patent application Ser. No. 09/266,641, filed Mar. 11, 1999, U.S. Pat. No. 6,127,550 which application is a continuation application of International Patent Application No. PCT/US97/15729, filed Sep. 10, 1997, which, in turn, claims priority of U.S. Provisional Application No. 60/026,005, filed Sep. 12, 1996, now abandoned.

FIELD OF THE INVENTION

This invention is directed to new methods for stereospecifically preparing [(1-optionally substituted aryl)- or (1-optionally substituted heteroaryl)]-2-substituted ethyl-2-amines, having chirality at the 2-position.

The invention is directed also to new intermediates that are useful for preparing substituted ethyl-2-amines.

The substituted ethyl-2-amines, and intermediate compounds therefor, are useful as intermediates in the synthesis of cardiovascular agents, including antihypertensive agents, anti-ischemic agents, cardioprotective agents which ameliorate ischemic injury or myocardial infarct size consequent to myocardial ischemia, and antilipolytic agents which reduce plasma lipid levels, serum triglyceride levels, and plasma cholesterol levels.

For example, the substituted ethyl-2-amines are useful as intermediates in the preparation of antihypertensive and anti-ischemic heterocyclyl adenosine derivatives and analogues as disclosed in U.S. Pat. No. 5,364,862. They are useful also in the preparation of $N_9$-cyclopentyl-substituted adenine derivatives reported to be adenosine receptor ligands, and to be useful in treating cardiovascular conditions such as hypertension, thrombosis and atherosclerosis, and also in treating central nervous system conditions comprising psychotic conditions such as schizophrenia, and convulsive disorders such as epilepsy, as disclosed in U.S. Pat. No. 4,954,504. They are useful also in the preparation of N-6 and 5'-N substituted carboxamidoadenosine derivatives which have beneficial cardiovascular and antihypertensive activity as reported in U.S. Pat. No. 5,310,731.

REPORTED DEVELOPMENTS

Stereospecific preparation of chiral optionally substituted heteroaryl-2-substituted ethyl 2-amines by reaction of heteroaryl anions with 2-substituted ethylene oxides, and subsequent stereospecific conversion of the resulting chiral ethyl alcohol to the amine has been reported by Spada et al., in U.S. Pat. No. 5,364,862.

Facilitation of acidolytic cleavage reactions, for example the removal of various protecting groups, in the presence of electrophilic scavengers has been reported. Deprotection of $N^G$-mesitylene-2-sulfonylarginine is reported by Yajima et al., *Chem. Pharm. Bull.* 26 (12) 3752–3757 (1978). Removal of the protecting group of O-benzyl serine, threonine, and tyrosine, and deprotection of $N^e$-benzyloxycarbonyllysine is reported by Kiso et al., *Chem. Pharm. Bull.* 28 (2) 673–676 (1980). Deprotection procedures for the p-toluenesulfonyl and p-methoxybenzenesulfonyl groups from the $N^{im}$ function of histidine is reported by Kitagawa et al., *Chem. Pharm. Bull.* 28 (3) 926–931 (1980).

SUMMARY OF THE INVENTION

The present invention is directed to methods for stereospecifically preparing [(1-optionally substituted aryl)- or (1-optionally substituted heteroaryl)]-2-substituted ethyl-2-amines, having chirality at the 2-position, comprising reacting a 2-amino-2-substituted ethyl alcohol, having chirality at the 2-position, with an [(optionally substituted aryl)- or (trihalomethyl) sulfonyl]-halide or anhydride in the presence of a base to form an [(N-arylsulfonyl)- or (N-trihalomethylsulfonyl)]-2-substituted aziridine having chirality at the 2-position.

DETAILED DESCRIPTION

As used above, and throughout the description of this invention, the following terms, unless otherwise indicated, shall be understood to have the following meanings:

"Aryl" means phenyl or naphthyl.

"Optionally substituted aryl" means an aryl group which may be substituted with one or more aryl group substituents. Examples of aryl group substituents include alkyl, alkoxy, amino, aryl, heteroaryl, trihalomethyl, nitro, carboxy, carboalkoxy, carboxyalkyl, cyano, alkylamino, halo, hydroxy, hydroxyalkyl, mercaptyl, alkylmercaptyl, and carbamoyl. Preferred aryl group substituents include halo, hydroxy, alkyl, aryl, alkoxy, trihalomethyl, cyano, nitro, and alkylmercaptyl.

"Heteroaryl" means about a 4 to about a 10 membered aromatic ring structure in which one or more of the atoms in the ring is an element other than carbon, e.g., N, O or S. Examples of heteroaryl groups include pyridyl, pyridazinyl, pyrimidinyl, isoquinolinyl, quinolinyl, quinazolinyl, imidazolyl, pyrrolyl, furanyl, thienyl, thiazolyl, and benzothiazolyl. A preferred heteroaryl group is thienyl.

"Optionally substituted heteroaryl" means that the heteroaryl group may be substituted by one or more heteroaryl group substituents. Examples of heteroaryl group substituents include alkyl alkoxy, alkylamino, aryl, carbalkoxy, carbamoyl, cyano, halo, heteroaryl, trihalomethyl, hydroxy, mercaptyl, alkylmercaptyl and nitro. Preferred heteroaryl group substituents include halo, hydroxy, alkyl, aryl, alkoxy, trihalomethyl, cyano, nitro, and alkylmercaptyl.

"Halogen" ("halo", "halide") means chlorine (chloro, chloride), fluorine (fluoro, fluoride), bromine (bromo, bromide) or iodine (iodo, iodide). "Alkyl" means a saturated aliphatic hydrocarbon group which may be straight or branched and have about 1 to about 20 carbon atoms in the chain. Preferred alkyl groups may be straight or branched and have about 1 to about 10 carbon atoms in the chain. Lower alkyl means an alkyl group which may be straight or branched having about 1 to about 6 carbon atoms, such as methyl, ethyl, propyl or tert-butyl. Branched means that a lower alkyl group is attached to a linear alkyl chain.

"Aralkyl" means an alkyl group substituted by an aryl group. "Optionally substituted aralkyl" means that the aryl group of the aralkyl group may be substituted with one or more aryl group substituents.

"Heteroaralkyl" means an alkyl group substituted by a heteroaryl group. "Optionally substituted heteroaralkyl" means that the heteroaryl group or the heteroaralkyl group may be substituted with one or more aryl group substituents.

"Electrophilic scavenger" means an agent that can have a promoting effect on acidolytic cleavage reactions, for example, as described by Yajima et al., *Chem. Pharm. Bull.* 26 (12) 3752–3757 (1978), Kiso et al., *Chem. Pharm. Bull.* 28 (2) 673–676 (1980), and Kitagawa et al., *Chem. Pharm. Bull.* 28(3)926–931 (1980).

An embodiment according to the invention is directed to the reaction of a 2-amino-2-substituted ethyl alcohol with a sulfonyl halide or anhydride, preferably in the presence of an aprotic organic solvent. Aprotic organic solvents which are suitable for the reaction include aprotic organic ethers, aromatic hydrocarbons, heteroaromatic hydrocarbons, aliphatic hydrocarbons, and aprotic organic amides. More particularly, examples of suitable aprotic organic solvents include diethyl ether, tert-butyl methyl ether, isopropyl methyl ether, diisopropyl ether, tetrahydrofuran, tetrahydropyran, and dioxan. In a special embodiment of methods according to the invention, the preferred aprotic organic solvent is tert-butyl methyl ether.

The reaction with the sulfonyl halide or anhydride takes place preferably at a temperature in the range of from about 25° C. to about 90° C.; more preferably from about 25° C. to about 40° C.

Suitable sulfonyl halides and anhydrides include phenyl-, tol-4-yl-, 2,4,6-trimethylphenyl-, 2,4-dimethylphenyl-, 4-methoxyphenyl-, 4-nitrophenyl-, 4-bromophenyl-, naphth-1-yl-, naphth-2-yl-, and trifluoromethyl-sulfonyl chloride and anhydride. In a special embodiment of methods according to the invention, a preferred sulfonyl chloride is p-toluenesulfonyl chloride (i.e., tol-4-yl sulfonyl chloride).

According to the invention, the reaction of the 2-amino-2-substituted ethyl alcohol with the sulfonyl halide or anhydride takes place in the presence of a base. Bases which are suitable for the reaction include aqueous alkali metal hydroxides, aqueous alkali metal carbonates, and aprotic organic amines. More particularly, examples of suitable alkali metal hydroxides include sodium hydroxide, potassium hydroxide, and lithium hydroxide; examples of suitable alkali metal carbonates include potassium carbonate, sodium carbonate, and cesium carbonate; and examples of suitable aprotic organic amines include triethylamine, diisopropyl ethyl amine, N-methylmorpholine, and pyridine. In a special embodiment of methods according to the invention, a preferred base is aqueous sodium hydroxide.

Another embodiment according to the invention is directed to the reaction of the [(N-arylsulfonyl)- or (N-trihalomethylsulfonyl)]-2-substituted aziridine having chirality at the 2-position, which is formed from the reaction of the 2-amino-2-substituted ethyl alcohol with the sulfonyl halide or anhydride, with an [(optionally substituted aryl)- or (optionally substituted heteroaryl)] lithium compound to form the lithium salt of an [(N-optionally substituted aryl)- or (N-trihalomethyl)sulfonyl]-1-[(optionally substituted aryl)- or (optionally substituted heteroaryl)]-2-substituted alkyl-2-amine having chirality at the 2-position. In a special embodiment of the invention, the lithium salt formed in the reaction is isolated as a solid.

Organolithium compounds may exist as tetramers, hexamers, and higher aggregates in hydrocarbon and ether solvents, as described, for example, by Carey, F. A., and Sundberg, Richard J., *Advanced Organic Chemistry*, Plenum Press, New York (2d ed. 1984), and Fraenkel et al., *J Am. Chem. Soc.* 102, 3345 (1980). Formation by methods according to the invention of such aggregates of the lithium salts, and the aggregates so-formed are contemplated by and included in the invention.

The reaction to form lithium salt takes place preferably in an aprotic organic solvent. Aprotic organic solvents which are suitable for the reaction include aprotic organic ethers, aliphatic hydrocarbons, and aromatic hydrocarbons. In a special embodiment of methods according to the invention, a preferred aprotic organic solvent is an aprotic organic ether and, more particularly, tert-butyl methyl ether.

The formation of the lithium salt takes place preferably at about −80° C. to about 50° C.; more preferably at about −40° C. to about 50° C.

Yet another embodiment according to the invention is directed to the treatment of the lithium salt of an [(N-optionally substituted aryl)- or (N-trihalomethyl)sulfonyl]-1-[(optionally substituted aryl)- or (optionally substituted heteroaryl)]-2-substituted alkyl-2-amine having chirality at the 2-position with one or more strong acids in the presence of an electrophilic scavenger. This treatment takes place preferably at a temperature range of about 45° C. to about reflux.

Strong acids which are suitable for the treatment include methanesulfonic acid, trifluoroacetic acid, trifluoromethanesulfonic acid, trichloromethane sulfonic acid, trichloroacetic acid, sulfuric acid, hydrochloric acid, hydrobromic acid, and phosphoric acid. In a special embodiment of the invention, the treatment takes place preferably in a mixture of strong acids; more preferably in a mixture of methanesulfonic acid and trifluoroacetic acid.

Electrophilic scavengers which are suitable for the treatment include anisole, thioanisole, diphenyldisulfide, phenylbenzylsulfide, trimethoxybenzene, m-cresol, and 1,2-ethanediol. In a special embodiment according to the invention, a preferred electrophilic scavenger is thioanisole.

A preferred embodiment according to the invention is a method for preparing a compound of Formula I,

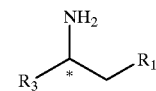

Formula I wherein
* indicates a chiral carbon atom,
$R_1$ is optionally substituted aryl, or optionally substituted heteroaryl; and
$R_3$ is optionally substituted alkyl, optionally substituted aryl, optionally substituted aralkyl, optionally substituted heteroaryl, or optionally substituted heteroaralkyl, comprising reacting a compound of Formula II

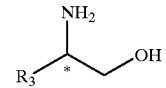

Formula II with a compound of Formula III $$R_2\text{—}SO_2\text{—}R'$$  Formula III wherein
R' is halo or $OSO_2R_2$; and
$R_2$ is optionally substituted aryl, or trihalomethyl,
in the presence of a base to form an aziridine compound of Formula IV.

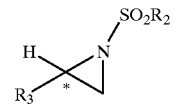

Formula IV

A further preferred embodiment of the present invention is the method of preparing a compound of Formula I wherein $R_1$ is optionally substituted heteroaryl; more preferably wherein $R_1$ is 3-chlorothien-2-yl.

Another further preferred embodiment of the invention is the method for preparing the compound of Formula I wherein $R_3$ is alkyl; more preferably wherein $R_3$ is ethyl.

Another preferred embodiment according to the invention is a method for preparing a compound of Formula I, comprising reacting the aziridine of Formula IV with a compound of formula Li—$R_1$ to form a lithium compound of Formula V,

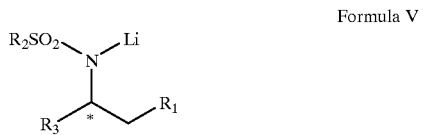

Formula V or an aggregate thereof.

Another preferred embodiment according to the invention is a method for preparing a compound of Formula I, comprising treating the lithium compound of Formula V with a strong acid or mixture of strong acids in the presence of an electrophilic scavenger.

Preferred embodiments according to the invention are illustrated in Scheme I.

Scheme I

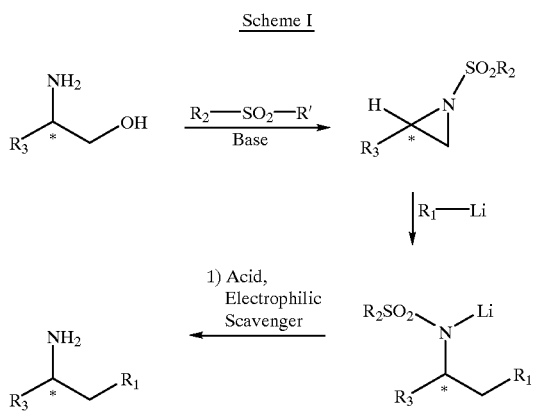

If it is necessary or desirable to prevent cross-reaction between chemically active substituents (for example, any aryl or heteroaryl group substituents) during the reactions according to the invention, the substituents may be protected by standard blocking groups which may be subsequently removed or retained, as required, by known methods, to afford the desired product. (See, for example, Green, *Protective Groups in Organic Synthesis*, Wiley, New York (1982).) Selective protection or deprotection also may be necessary or desirable to allow conversion or removal of existing substituents, or to allow subsequent reaction to afford the final desired product.

The present invention is directed also to intermediates to [(1-optionally substituted aryl)- or (1-optionally substituted heteroaryl)]-2-substituted ethyl-2-amines.

A compound embodiment according to the invention is the [(N-arylsulfonyl)- or (N-trihalomethylsulfonyl)]-2-substituted aziridine having chirality at the 2-position, formed by the reaction of the of the 2-amino-2-substituted ethyl alcohol with the sulfonyl halide or anhydride according to the method of the invention. A preferred embodiment of said aziridine is the compound of Formula IV. A special embodiment of said aziridine includes 1-p-toluenesulfonyl-2(R)-ethylaziridine.

Another compound embodiment according invention is the lithium salt of an [(N-optionally substituted aryl)- or (N-trihalomethyl)sulfonyl]-1-[(optionally substituted aryl)- or (optionally substituted heteroaryl)]-2-substituted alkyl-2-amine having chirality at the 2-position formed by the reaction of the aziridine with an [(optionally substituted aryl)- or (optionally substituted heteroaryl)] lithium compound according to the method of the invention. A preferred embodiment of this lithium salt is the compound of Formula V. A special embodiment of the lithium salt is (R)-1-(3-chlorothien-2-yl)-2-butyltoluenesulfonamide lithium salt.

The present invention is further explained, but is in no way limited, by the following examples.

EXAMPLE 1

Preparation of 1-p-toluenesulfonyl-2(R)-ethylaziridine

R-(−)-2-amino-1-butanol (99.96 g, 105 mL) and tert-butyl methyl ether (TBME) (277 g, 366 mL) are combined under a nitrogen atmosphere. This mixture is stirred for several minutes and 10 N aqueous sodium hydroxide (449 mL) is added over a period of about 10 minutes. The reaction mixture is cooled to below 10° C. and a solution of p-toluene sulfonyl chloride (TsCl) (464 g) in TBME (711 g) is added over a period of about 50 minutes, maintaining the temperature of the reaction mixture at or below 32° C. After the addition is complete, the mixture is stirred for about 30 minutes at 40° C., and water (900 mL) is added while cooling the mixture to 25° C. The layers are separated and the organic layer washed sequentially with water (150 g) and 25% aqueous sodium chloride solution (300 g). Toluene (450 g) is added to the organic layer, and the mixture distilled under reduced pressure, maintaining the temperature of the mixture at or below 45° C., until the water content of the mixture is below about 0.1%. The resulting solution is used, without further treatment, for the preparation described in Example 2.

EXAMPLE 2

Preparation of (R)-1-(3-chlorothien-2-yl)-2-butyltoluenesulfonamide Lithium Salt Under a nitrogen atmosphere, a solution of 3-chlorothiophene (48.75 g) in TBME (291 g) is cooled to −10° C., and 2.5 M n-butyllithium in hexanes (151.3 mL) is added at such a rate that the reaction temperature is maintained between 0 and 5° C. After the addition is complete, the mixture is cooled to −5° C. and 1-p-toluenesulfonyl-2(R)-ethylaziridine (74.1 g, as a 56.9% (w/w) solution in TBME) is added at such a rate as to maintain the temperature of the reaction mixture below 9° C. (during which time a solid precipitates). After about 5 minutes the mixture is cooled to 0° C. and the precipitate is collected by vacuum filtration, washed with 0° C. TBME (60 mL), and dried in vacuo at about 40° C., to give (R)-1-(3-chlorothien-2-yl)-2-butyltoluenesulfonamide lithium salt, m.p. 372° C. (dec.). MS (FAB), m/z 350, 352 (100%), $^1$HNMR (200 Mhz, DMSO) δ 0.8 (t, 3H); 2.25 (s, 3H); 6.85 (d, 1H); 7.05 (d, 2H), 7.35 (d, 2H).

EXAMPLE 3

Preparation of (R)-1-(3-chlorothien-2-yl)-2-aminobutane (R)-1-(3-chlorothien-2-yl)-2-butyltoluenesulfonamide lithium salt (120 g) is added in one portion to trifluoroacetic acid (470 g) in a vessel equipped with a condenser and mechanical stirrer. The temperature of the mixture rises from about 25° C. to about 60° C. As the resulting solution is cooling, thioanisole (85.2 g) is added, followed by methanesulfonic acid (65.9 g). The reaction mixture is heated at 80° C. for about six hours. The mixture is cooled to 18° C. and toluene (600 mL) is added. 6M aqueous sodium hydroxide solution (820 mL) is then added portionwise, with stirring, maintaining the reaction temperature below 60° C. The layers are separated and the organic phase is washed with water until the pH of the wash is 9; then it is washed with brine. The organic solution is cooled to 18° C. and toluene (200 mL) is added, followed by concentrated hydrochloric acid (42 mL). The resulting slurry is distilled at about 47° C. at 180 mm Hg to azeotropically remove water. After about 200 mL of toluene/water had been removed, the mixture is cooled to 40° C., allowed to come to atmospheric pressure, then cooled to 15° C. over a 1 hour period. The solids which precipitate are collected by vacuum filtration, washed with 60 mL of toluene and dried in vacuo to give (R)-1-(3-chlorothien-2-yl)-2-aminobutane as the hydrochloride salt, m.p. 137.6° C. MS (EI), m/z 190, 192 (10%); $^1$HNMR (200 Mhz, DMSO) δ 0.9 (t, 3H); 1.6 (m, 2H); 7.05 (d, 1H); 7.6 (d, 2H), 8.35 (s, 2H).

What is claimed is:

1. A method for stereospecifically preparing a [(1-optionally substituted arylsoulfonyl)- or (1-optionally substituted heteroaryl)]-2-substituted ethyl-2-amine, having chirality at the 2-position, comprising reacting a 2-amino-2-substituted ethyl alcohol, having chirality at the 2-position, with an [(optionally substituted aryl)- or (trihalomethyl) sulfonyl]-halide or anhydride in the presence of a base to form an [(N-arylsulfonyl)- or (N-trihalomethylsulfonyl)]-2-substituted aziridine having chirality at the 2-position.

2. A method according to claim 1 further comprising reacting said aziridine with an [(optionally substituted arylsulfonyl)- or (optionally substituted heteroaryl)] lithium compound to form the lithium salt of an [(N-optionally substituted aryl)- or (N-trihalomethyl)sulfonyl]-1-[(optionally substituted aryl)- or (optionally substituted heteroaryl)]-2-substituted alkyl-2-amine having chirality at the 2-position.

3. A method according to claim 1 for preparing a compound of formula

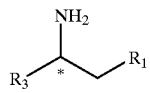

wherein

* indicates a chiral carbon atom, $R_1$ is optionally substituted aryl, or optionally substituted heteroaryl; and $R_3$ is optionally substituted alkyl, optionally substituted aryl, optionally substituted aralkyl, optionally substituted heteroaryl, or optionally substituted heteroaralkyl; comprising reacting a compound of formula

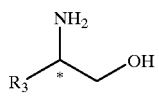

with a compound of formula

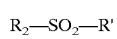

wherein

R' is halo or $OSO_2R_2$; and $R_2$ is optionally substituted aryl, or trihalomethyl, in the presence of a base to form an aziridine compound of formula.

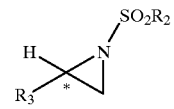

4. A method according to claim 3 further comprising reacting said aziridine compound with a compound of formula Li—$R_1$, to form a lithium compound of formula

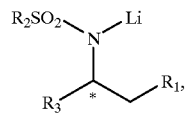

or an aggregate thereof, wherein $R_1$ is optionally substituted aryl, or optionally substituted heteroaryl;

$R_2$ is optionally substituted aryl, or trihalomethyl; and $R_3$ is optionally substituted alkyl, optionally substituted aryl, optionally substituted aralkyl, optionally substituted heteroaryl, or optionally substituted heteroaralkyl.

5. A method according to claim 3 wherein said reaction occurs in an aprotic organic solvent.

6. A method according to claim 5 wherein said aprotic organic solvent is tert-butyl methyl ether.

7. A method according to claim 3 wherein $R_2$—$SO_2$—R' is p-toluenesulfonyl chloride.

8. A method according to claim 3 wherein said reaction occurs at about 25° C. to about 90° C.

9. A method according to claim 3 wherein said reacting occurs at about 25° C. to about 40° C.

10. A method according to claim 3 wherein said base is selected from the group consisting of an aqueous alkali metal hydroxide, an aqueous alkali metal carbonate, and an aprotic organic amine.

11. A method according to claim 3 wherein said base is aqueous sodium hydroxide.

12. A method according to claim 3 wherein $R_1$ is optionally substituted heteroaryl.

13. A method according to claim 12 wherein $R_1$ is 3-chlorothien-2-yl.

14. A method according to claim 3 wherein $R_3$ is alkyl.

15. A method according to claim 14 wherein $R_3$ is ethyl.

16. A method according to claim 4 wherein reacting said aziridine compound occurs in a solvent selected from the group consisting of an aprotic organic ether, aliphatic hydrocarbon, and an aromatic hydrocarbon.

17. A method according to claim 16 wherein said reacting said aziridine compound occurs in tert-butyl methyl ether.

18. A method according to claim 4 further comprising isolating said lithium compound as a solid.

19. A method according to claim 4 wherein said reacting occurs at about −80° C. to about 50° C.

20. A method according to claim 19 wherein said reacting occurs at about −40° C. to about 50° C.

21. A [(N-arylsulfonyl)- or (N-trihalomethylsulfonyl)]-2-substituted aziridine having chirality at the 2-position.

22. The aziridine compound according to claim 21 which is 1-p-toluenesulfonyl-2(R)-ethylaziridine.

23. A lithium salt of an [(N-optionally substituted aryl)- or (N-trihalomethyl)sulfonyl]-1-[(optionally substituted aryl)- or (optionally substituted heteroaryl)]-2-substituted alkyl-2-amine, having chirality at the 2-position.

24. The lithium salt according to claim 23 of formula

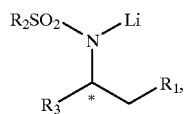

or an aggregate thereof,
wherein
- $R_1$ is optionally substituted aryl, or optionally substituted heteroaryl;
- $R_2$ is optionally substituted aryl, or trihalomethyl; and
- $R_3$ is optionally substituted alkyl, optionally substituted aryl, optionally substituted aralkyl, optionally substituted heteroaryl, or optionally substituted heteroaralkyl.

25. The lithium compound according to claim 24 which is (R)-1-(3-chlorothien-2-yl)-2-butyltoluenesulfonamide lithium salt.

* * * * *

UNITED STATES PATENT AND TRADEMARK OFFICE
CERTIFICATE OF CORRECTION

PATENT NO.    : 6,433,172 B1
DATED         : August 13, 2002
INVENTOR(S)   : Grondard et al.

It is certified that error appears in the above-identified patent and that said Letters Patent is hereby corrected as shown below:

<u>Title page, Item [54], and Column 1, line 1,</u>
Title reads "STEROESPECIFIC" and should read as -- STEREOSPECIFIC --.

<u>Column 7,</u>
Line 24, reads "optionally substituted arylsoulfonyl…" and should read as -- optionally substituted arylsulfonyl --.

Signed and Sealed this

Twenty-fifth Day of March, 2003

JAMES E. ROGAN
*Director of the United States Patent and Trademark Office*